(12) United States Patent
Lattner et al.

(10) Patent No.: US 7,598,197 B2
(45) Date of Patent: Oct. 6, 2009

(54) CATALYST COOLING PROCESSES UTILIZING STEAM SUPERHEATING

(75) Inventors: James R. Lattner, Seabrook, TX (US); Christopher L. Becker, Russell, KS (US); James H. Beech, Jr., Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 888 days.

(21) Appl. No.: 11/050,574

(22) Filed: Feb. 3, 2005

(65) Prior Publication Data
US 2006/0135358 A1   Jun. 22, 2006

Related U.S. Application Data

(60) Provisional application No. 60/638,734, filed on Dec. 22, 2004.

(51) Int. Cl.
B01J 38/12 (2006.01)
B01J 38/16 (2006.01)

(52) U.S. Cl. .............. 502/38; 502/20; 502/51; 502/55; 502/514

(58) Field of Classification Search ........... 502/20, 502/55, 56, 208, 214, 514; 585/640, 910, 585/911
See application file for complete search history.

(56) References Cited

U.S. PATENT DOCUMENTS

| | | | |
|---|---|---|---|
| 2,488,027 A | 11/1949 | Page | 196/52 |
| 2,755,782 A | 7/1956 | Campbell et al. | 122/459 |
| 2,853,455 A | 9/1958 | Campbell et al. | 252/417 |
| 2,926,143 A | 2/1960 | Leland | 252/417 |
| 3,997,428 A * | 12/1976 | McKenna | 208/78 |
| 4,009,121 A | 2/1977 | Luckenbach | 252/417 |
| 4,160,743 A | 7/1979 | Kelley | 252/411 R |
| 4,423,274 A | 12/1983 | Daviduk et al. | |
| 4,563,264 A | 1/1986 | Weiss et al. | 208/11 R |
| 4,563,267 A | 1/1986 | Graham et al. | 208/159 |
| 5,700,432 A | 12/1997 | Tanaka et al. | 422/146 |
| 6,023,005 A | 2/2000 | Lattner et al. | 585/639 |
| 6,245,703 B1 * | 6/2001 | Kuechler et al. | 502/22 |

(Continued)

FOREIGN PATENT DOCUMENTS

DE   3412482   10/1985

(Continued)

OTHER PUBLICATIONS

Abstract—Campbell, O.F. et al, "Carbon Monoxide Boiler and Fluidized-Bed Superheater on Sinclair Refining Company's New Fluid Unit at the Houston Refinery", Transactions of the ASME (1955), 77, pp. 927-938.

(Continued)

Primary Examiner—In Suk Bullock
(74) Attorney, Agent, or Firm—Kevin M. Faulkner; Frank E. Reid; David M. Weisberg

(57) ABSTRACT

This invention provides processes, systems and devices for cooling catalyst, preferably regenerated catalyst, by superheating steam and boiling water. The inventive process advantageously provides ideal cooling conditions while ensuring minimal hydrothermal deactivation of the catalyst during the cooling process. The invention is particularly well-suited for cooling catalyst in an oxygenate to olefins reaction system.

20 Claims, 7 Drawing Sheets

U.S. PATENT DOCUMENTS

2004/0102668 A1    5/2004   Lumgair, Jr. et al.
2005/0043577 A1    2/2005   Beech et al. ................ 585/640

FOREIGN PATENT DOCUMENTS

EP      0108482      5/1984

GB      1548414      7/1979

OTHER PUBLICATIONS

U.S. Appl. No. 10/812,142, filed Mar. 29, 2004, "Heat Recovery Technique For Catalyst Regenerator Flue Gas", Inventors: Cor F. van Egmond, James H. Beech, Jr., Hans Klemm, and Kyle Castaldy.

* cited by examiner

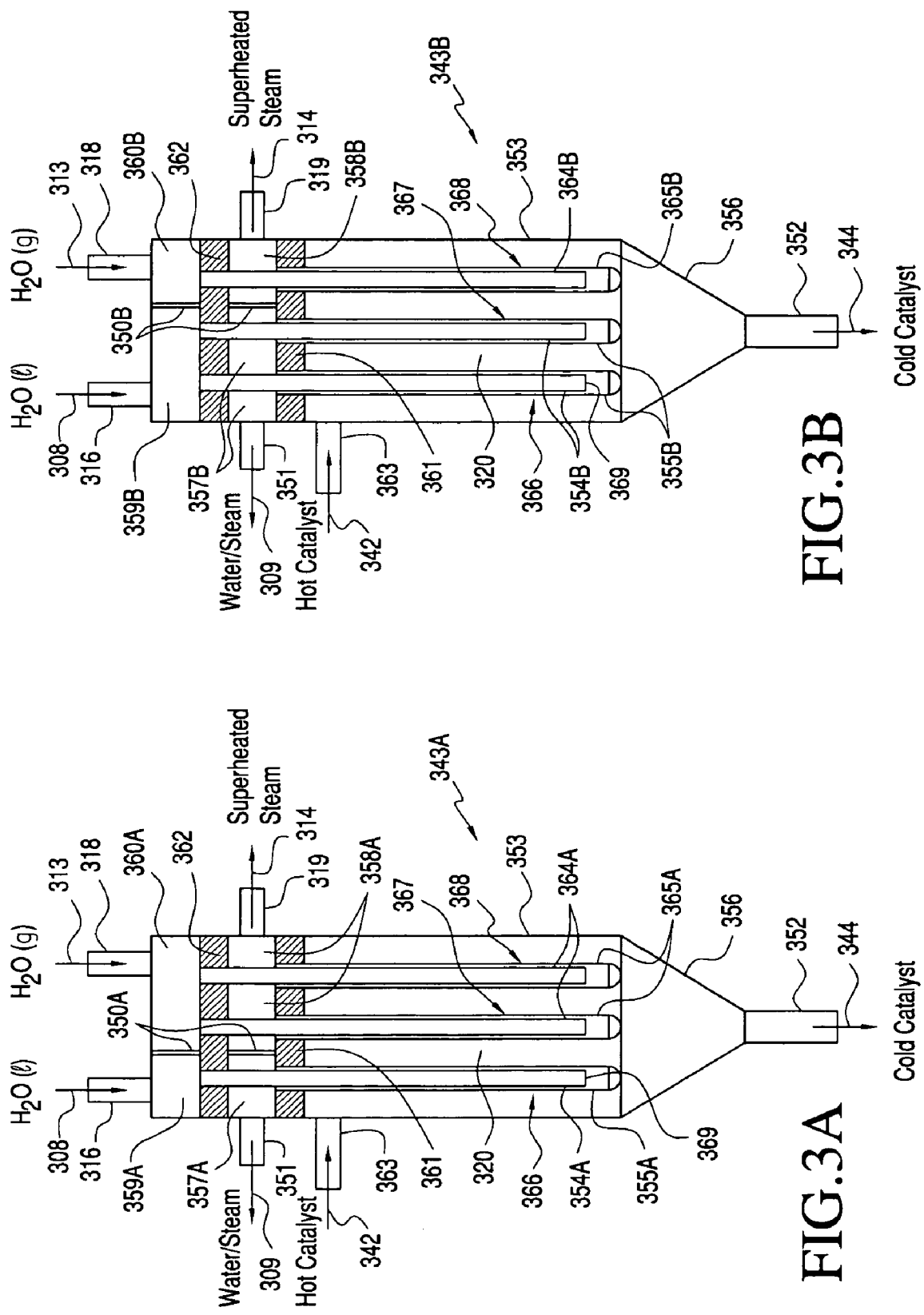

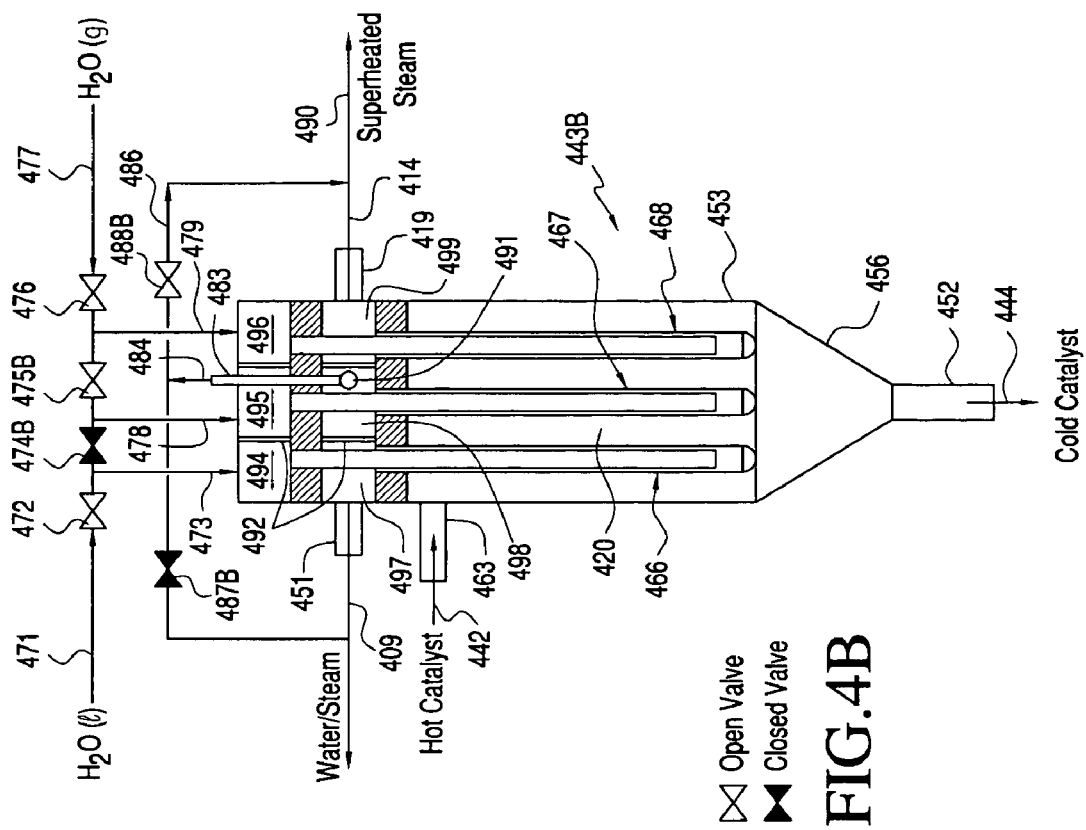
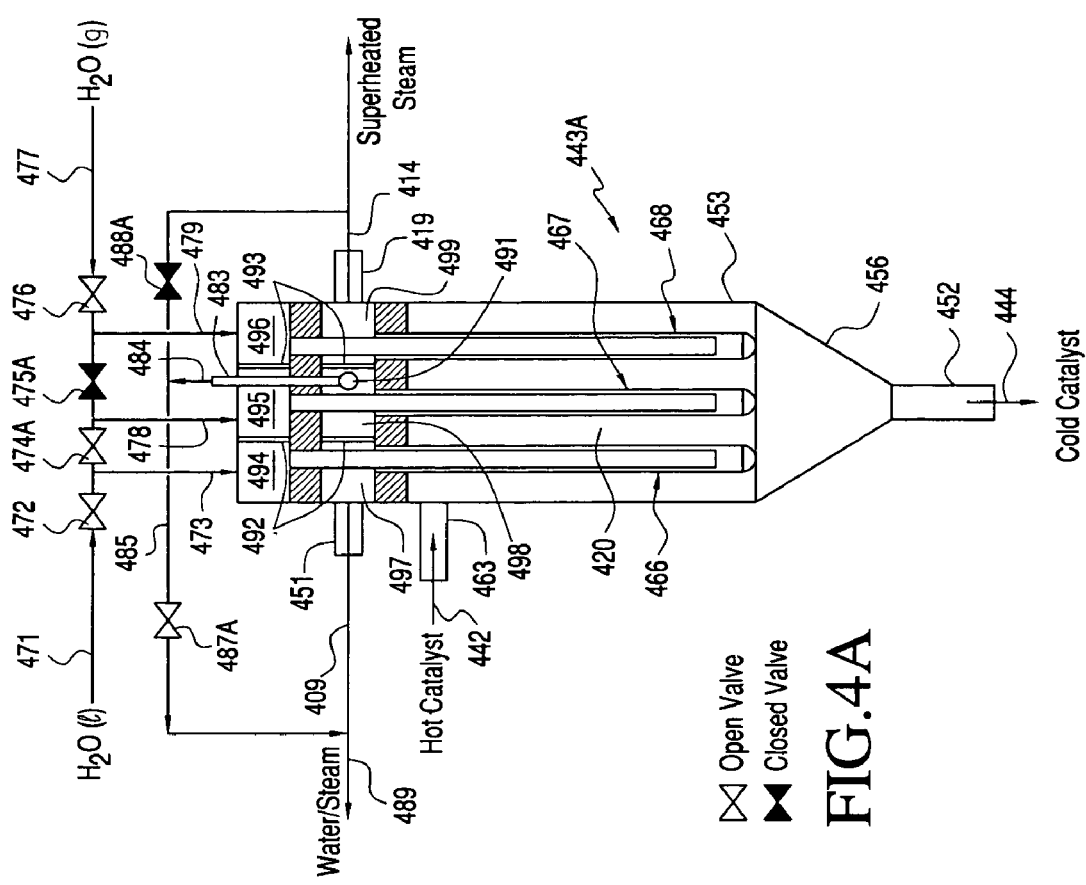

CATALYST COOLING PROCESSES UTILIZING STEAM SUPERHEATING

CROSS-REFERENCE TO RELATED APPLICATIONS

The present application claims the benefit of U.S. Provisional Application No. 60/638,734, filed Dec. 22, 2004, said application hereby fully incorporated by reference.

FIELD OF THE INVENTION

The present invention relates to cooling catalyst. More particularly, the invention relates to cooling an oxygenate to olefin catalyst using steam superheating.

BACKGROUND OF THE INVENTION

Light olefins, defined herein as ethylene and propylene, serve as feeds for the production of numerous chemicals. Olefins traditionally have been produced by petroleum cracking, for example, by fluidized catalytic cracking (FCC). Because of the limited supply and/or the high cost of petroleum sources, the cost of producing olefins from petroleum sources has increased steadily.

In addition to cracking petroleum products, the petrochemical industry has known for some time that oxygenates, especially alcohols, are convertible into light olefins. The preferred conversion process is generally referred to as an oxygenate to olefin (OTO) reaction process. Specifically, in an OTO reaction process, an oxygenate contacts a molecular sieve catalyst composition under conditions effective to convert at least a portion of the oxygenate to light olefins. When methanol is the oxygenate, the process is generally referred to as a methanol to olefin (MTO) reaction process. Methanol is a particularly preferred oxygenate for the synthesis of ethylene and/or propylene In an OTO conversion process carbonaceous material (coke) is deposited on the molecular sieve catalysts used to catalyze the conversion process. Excessive accumulation of these carbonaceous deposits will interfere with the catalyst's ability to promote the reaction. In order to avoid unwanted build-up of coke on molecular sieve catalysts, the OTO and MTO processes incorporate a second step comprising catalyst regeneration. During regeneration, the coke is at least partially removed from the catalyst by combustion with oxygen, which restores the catalytic activity of the catalyst and forms a regenerated catalyst. The regenerated catalyst then may be reused to catalyze the OTO conversion process.

In conventional regeneration vessels, coked catalyst is directed from a reactor to a catalyst regenerator. In a catalyst regenerator, a regeneration medium, usually oxygen, enters the regenerator, and coke is removed from the coked catalyst by combustion with the regeneration medium to form regenerated catalyst and gaseous byproducts. The bulk of the regenerated catalyst from the regenerator is returned to the reactor. The gaseous byproducts are forced out an exhaust outlet oriented in the upper section of the catalyst regenerator.

The combustion of the carbonaceous deposits from molecular sieve catalyst compositions during catalyst regeneration is an exothermic process. The exothermic nature of catalyst regeneration presents a unique problem in OTO regeneration systems because the OTO reaction process is operated such that the level of carbonaceous deposits on the molecular sieve catalyst composition is higher than the level typically found on catalyst compositions used in FCC processes. As a result, the amount of heat liberated from the OTO molecular sieve catalyst compositions during catalyst regeneration is significantly greater than the amount of heat liberated from the regeneration of catalysts in FCC processes. The significant amount of heat liberated in regenerating OTO catalyst compositions may exceed the material tolerances of the materials used to form the catalyst regenerator. The heat can also damage the catalyst particles themselves. It is therefore desirable to provide processes and systems for controlling the temperature of a regeneration vessel in an OTO reaction system.

SUMMARY OF THE INVENTION

The present invention is directed to processes and systems for cooling catalyst, preferably catalyst in an oxygenate to olefins reaction system. In one embodiment, the invention is to a process comprising the step of: (a) cooling a hot catalyst by superheating steam and boiling water to form a cold catalyst. As used herein, the terms "hot catalyst," "cool catalyst," and "cold catalyst" are relative to one another and are not limited to any particular temperature ranges. For example, hot catalyst has a temperature greater than cool catalyst, which has a temperature greater than cold catalyst.

Preferably, step (a) occurs in one or more heat exchangers that are in fluid communication with a catalyst regenerator. Optionally, the cooling occurs in one or more heat exchangers comprising a first cooling surface and a second cooling surface, wherein the first cooling surface has a first surface area dedicated to superheating steam and the second cooling surface has a second surface area dedicated to boiling water. In this embodiment, the ratio of the first surface area to the second surface area can be adjusted. For example, the ratio optionally is adjustable by moving a baffle located within a side of the one or more heat exchangers that divides steam superheating service from boiling water service. Additionally or alternatively, the ratio is adjustable by dividing the one or more heat exchangers into a plurality of zones, wherein one or more of the zones can be piped into either steam superheating service or boiling water service. Additionally or alternatively, the ratio is adjustable by providing a plurality of heat exchangers, wherein one or more of the plurality of heat exchangers can be piped into either steam superheating service or boiling water service.

Optionally, the hot catalyst and the cold catalyst comprise a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, AEI/CHA intergrowths, mixtures thereof, and metal containing forms thereof.

Optionally, step (a) comprises cooling the hot catalyst by simultaneously superheating steam and boiling water to form the cold catalyst. The boiling and the superheating optionally occur in separate heat exchangers or in a single heat exchanger.

Step (a) optionally occurs at a pressure of from about 10 kPaa to about 10,000 kpaa, from about 50 kPaa to about 5,000 kPaa, or from about 100 kPaa to about 1,000 kpaa. Preferably, the pressure ranges from about 1,000 to about 5,000 kpaa. These pressures are on the cooling medium side (steam/water side) of the heat exchanger rather than the regenerator side.

The hot catalyst preferably has a temperature of from about 400° C. to about 1000° C., more preferably from about 500° C. to about 900° C., and most preferably from about 600° C. to about 800° C. The cold catalyst has a temperature that is less than the temperature of the hot catalyst. The cold catalyst also preferably has a temperature of greater than about 316° C., more preferably greater than about 343° C., and most preferably greater than about 371° C. By maintaining the cold catalyst at a temperature greater than 316° C., hydrothermal deactivation can be minimized.

Optionally, the hot catalyst that is cooled in step (a) is received from a catalyst regenerator and the cold catalyst is returned to the catalyst regenerator.

In another embodiment, the invention is to a process for cooling catalyst in an oxygenate to olefins reaction system, wherein the process comprises the step of: (a) cooling a hot catalyst by superheating steam to form a cool catalyst; and (b) cooling the cool catalyst by boiling water to form a cold catalyst.

The cooling in step (a) preferably occurs in one or more first heat exchangers comprising a first cooling surface and the cooling in step (b) occurs in one or more second heat exchangers comprising a second cooling surface, wherein the first cooling surface has a first surface area dedicated to superheating steam and the second cooling surface has a second surface area dedicated to boiling water.

Optionally, the ratio of the first surface area to the second surface area can be adjusted. For example, the ratio optionally is adjustable by changing one or more of the first heat exchangers or one or more of the second heat exchangers from steam superheating service to boiling water service or from boiling water service to steam superheating service.

In this embodiment, the hot catalyst, the cool catalyst and the cold catalyst comprise a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, AEI/CHA intergrowths, mixtures thereof, and metal containing forms thereof.

Optionally, step (a) occurs before step (b). In this embodiment, steps (a) and (b) preferably occur in separate heat exchangers. Alternatively, steps (a) and (b) occur simultaneously. In this embodiment, steps (a) and (b) preferably occur in a single heat exchanger.

Steps (a) and (b) optionally occur at a pressure of from about 10 kPaa to about 10,000 kpaa, from about 50 kPaa to about 5,000 kPaa, or from about 100 kPaa to about 1,000 kPaa. Preferably, the pressure ranges from about 1,000 to about 5,000 kPaa. These pressures are on the cooling medium sides (steam/water side) of the heat exchangers rather than the regenerator side.

The hot catalyst optionally has a temperature of from about 400° C. to about 1000° C., preferably from about 500° C. to about 900° C., and most preferably from about 600° C. to about 800° C. The cold catalyst optionally has a temperature of greater than about 316° C., preferably greater than about 343° C., and most preferably greater than about 371° C.

Optionally, the hot catalyst that is cooled in step (a) is received from a catalyst regenerator and the cold catalyst is returned to the catalyst regenerator.

In another embodiment, the invention is directed to a process for regenerating catalyst, wherein the process comprises the steps of: (a) regenerating an at least partially coked catalyst particle to form a regenerated catalyst particle having a temperature greater than about 593° C.; and (b) cooling the regenerated catalyst particle by at least about 38° C. through superheating steam and boiling water, but to a temperature of no less than 316° C., at a regeneration pressure of less than about 10,343 kPag, to form a cold catalyst.

The cooling optionally occurs in one or more heat exchangers comprising a first cooling surface and a second cooling surface, wherein the first cooling surface has a first surface area dedicated to superheating steam and the second cooling surface has a second surface area dedicated to boiling water. The ratio of the first surface area to the second surface area optionally can be adjusted. For example, the ratio optionally is adjustable by moving a baffle located within a side of the one or more heat exchangers that divides steam superheating service from boiling water service. Additionally or alternatively, the ratio is adjustable by dividing the one or more heat exchangers into a plurality of zones, wherein one or more of the zones can be piped into either steam superheating service or boiling water service. Additionally or alternatively, the ratio is adjustable by providing a plurality of heat exchangers, wherein one or more of the plurality of heat exchangers can be piped into either steam superheating service or boiling water service.

In this embodiment, the regenerated catalyst and the cold catalyst optionally comprise a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, AEI/CHA intergrowths, mixtures thereof, and metal containing forms thereof.

Optionally, step (b) comprises the sub-steps of: (i) cooling the regenerated catalyst by superheating steam to form a cool catalyst; and (ii) cooling the cool catalyst by boiling water to form the cold catalyst. Sub-step (i) optionally occurs before sub-step (ii). In this embodiment, sub-steps (i) and (ii) preferably occur in separate heat exchangers. Alternatively, sub-steps (i) and (ii) occur simultaneously. In this embodiment, sub-steps (i) and (ii) preferably occur in a single heat exchanger.

Sub-steps (i) and (ii) optionally occur at a pressure of from about 10 kPaa to about 10,000 kpaa, from about 50 kPaa to about 5,000 kPaa, or from about 100 kPaa to about 1,000 kPaa. Preferably, the pressure ranges from about 1,000 to about 5,000 kpaa. These pressures are on the cooling medium side (steam/water side) of the heat exchanger(s) rather than the regenerator side.

Optionally, The regenerated catalyst has a temperature of from about 400° C. to about 1000° C., preferably from about 500° C. to about 900° C., and most preferably from about 600° C. to about 800° C. The cold catalyst optionally has a temperature of greater than about 316° C., preferably greater than about 343° C., and most preferably greater than about 371° C.

Optionally, the process further comprises the step of: (c) directing the cold catalyst back to the catalyst regenerator.

BRIEF DESCRIPTION OF THE DRAWINGS

This invention will be better understood by reference to the Detailed Description of the Invention when taken together with the attached drawings, wherein:

FIG. 3A illustrates a catalyst cooler in a first configuration according to another embodiment of the present invention;

FIG. 3B illustrates a catalyst cooler in a second configuration according to another embodiment of the present invention;

FIG. 4A illustrates a catalyst cooler in a first configuration according to another embodiment of the present invention;

FIG. 4B illustrates a catalyst cooler in a second configuration according to another embodiment of the present invention;

DETAILED DESCRIPTION OF THE INVENTION

A. Introduction

Figure 1:
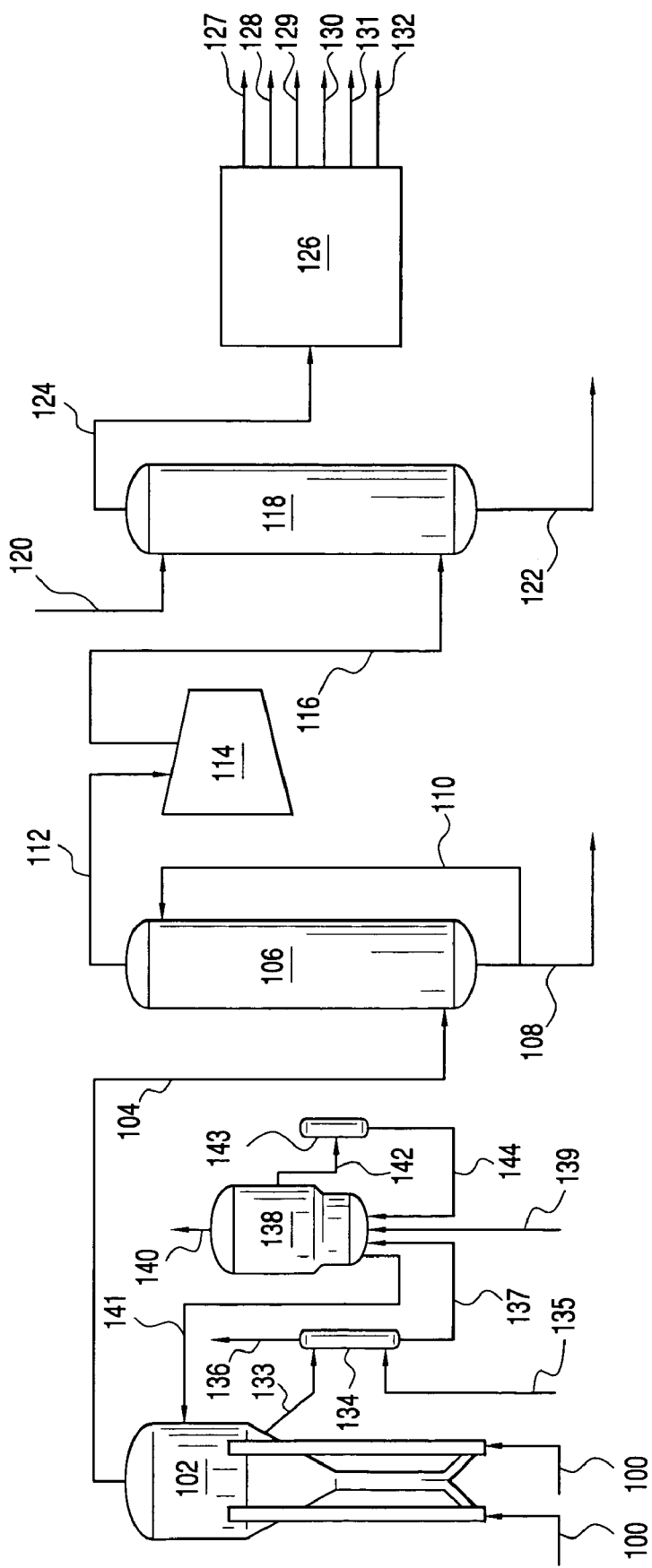
FIG. 1 illustrates a flow diagram illustrating an OTO reaction system and catalyst regeneration system.

The present invention provides processes, systems and devices for cooling catalyst particles. In a preferred embodiment, the catalyst particles cooled according to the present invention are derived from a catalyst regenerator in an oxygenate to olefins (OTO) reaction system. In one embodiment, the invention is to a process for cooling catalyst, wherein the process comprises the step of: (a) cooling a hot catalyst by superheating steam and boiling water to form a cold catalyst. By cooling the catalyst particles through superheating steam in conjunction with boiling water, the catalyst particles cooled by the processes, systems and devices of the present invention can be maintained at a temperature of no less than 316° C. By maintaining the temperature of the cooled catalyst particles at or above 316° C., hydrothermal deactivation of the catalyst particles can be advantageously minimized. Additionally, catalyst cooler duty can be decreased, for example during start up operations, shut down operations or during emergency situations, while maintaining the cold catalyst formed by the process of the present invention above the minimum threshold temperature.

B. Oxygenate to Olefins Reaction Systems

The present invention, in one embodiment, provides processes and systems for cooling catalyst particles. Preferably, the catalyst particles to be cooled are derived from an OTO reaction system, which is discussed in more detail in this section. As used herein, "reaction system" means a system comprising a reactor, a catalyst cooler, optionally a catalyst regenerator, and optionally a catalyst stripper. The reactor comprises a reaction unit, which defines a reaction zone, and optionally a disengaging unit, which defines a disengaging zone.

Molecular sieve catalyst compositions are used to convert oxygenate compounds to light olefins. Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. Preferably, the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof. Additionally or alternatively, the molecular sieve comprises an aluminophosphate (AlPO) molecular sieve. Preferred AlPO molecular sieves include AlPO-5, AlPO-11, AlPO-18, AlPO-31, AlPO-34, AlPO-36, AlPO-37, AlPO-46, AEI/CHA intergrowths, mixtures thereof, and metal containing forms thereof. Thus, the hot catalyst, the cool catalyst and/or the cold catalyst of the present invention preferably comprises a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, AEI/CHA intergrowths, mixtures thereof, and metal containing forms thereof.

The feedstock that is directed to an OTO reaction system optionally contains one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and more preferably from 1 to 4 carbon atoms, and most preferably methanol.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more organic compounds containing at least one oxygen atom. In the most preferred embodiment of the process of invention, the oxygenate in the feedstock comprises one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock comprises one or more of methanol, ethanol, DME, diethyl ether or a combination thereof.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In a preferred embodiment, the feedstock, which ideally comprises methanol, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as an oxygenate-to-olefins (OTO) reaction process. In an OTO process, typically an oxygenated feedstock, most preferably a methanol- and ethanol-containing feedstock, is converted in the presence of a molecular sieve catalyst composition into one or more olefins, preferably and predominantly, ethylene and/or propylene, referred to herein as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677, 242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. Pat. No. 7,102,050 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol, DME, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. Pat. No. 6,552,240, which is herein incorporated by reference.

FIG. 1 shows an exemplary OTO reaction system. In the figure, an oxygenate such as methanol is directed through lines 100 to an OTO fluidized reactor 102 wherein the oxygenate is converted to light olefins and various by-products which are yielded from the fluidized reactor 102 in an olefin-containing stream in line 104. The olefin-containing stream in line 104 optionally comprises methane, ethylene, ethane, propylene, propane, various oxygenate byproducts, C4+ olefins, water and hydrocarbon components. The olefin-containing stream in line 104 is directed to a quench unit or quench tower 106 wherein the olefin-containing stream in line 104 is cooled and water and other readily condensable components are condensed.

The condensed components, which comprise water, are withdrawn from the quench tower 106 through a bottoms line 108. A portion of the condensed components are recycled through a line 110 back to the top of the quench tower 106. The components in line 110 preferably are cooled in a cooling unit, e.g., heat exchanger (not shown), so as to provide a cooling medium to cool the components in quench tower 106.

An olefin-containing vapor is yielded from the quench tower 106 through overhead stream 112. The olefin-containing vapor is compressed in one or more compressors 114 and the resulting compressed olefin-containing stream is optionally passed through line 116 to a water absorption unit 118. Methanol is preferably used as the water absorbent, and is fed to the top portion of the water absorption unit 118 through line 120. Methanol and entrained water, as well as some oxygenates, are separated as a bottoms stream through line 122. The light olefins are recovered through overhead line 124. Optionally, the light olefins are sent to an additional compressor or compressors (not shown), and then are input to a separation system 126, which optionally comprises one or more separation units such as distillation columns, absorption units, and/or adsorption units.

The separation system 126 separates the components contained in the overhead line 124. Thus, separation system 126 forms a light ends stream 127, optionally comprising methane, hydrogen and/or carbon monoxide; an ethylene-containing stream 128 comprising mostly ethylene; an ethane-containing stream 129 comprising mostly ethane; a propylene-containing stream 130 comprising mostly propylene; a propane-containing stream 131 comprising mostly propane; and one or more byproduct streams, shown as line 132, comprising one or more of the oxygenate byproducts, provided above, heavy olefins, heavy paraffins, and/or absorption mediums utilized in the separation process. Separation processes that may be utilized to form these streams are well-known and are described, for example, in pending U.S. patent Application Nos. 2003/0199721; and 2003/0199724; and U.S. Pat. Nos. 7,074,971; and 7,214,846, the entireties of which are incorporated herein by reference.

FIG. 1 also illustrates a catalyst regeneration system, which is in fluid communication with fluidized reactor 102. As shown, at least a portion of the catalyst compositions contained in fluidized reactor 102 are withdrawn and transported, preferably in a fluidized manner, in conduit 133 from the fluidized reactor 102 to a catalyst stripper 134. In the catalyst stripper 134, the catalyst compositions contact a stripping medium, e.g., steam and/or nitrogen, under conditions effective to remove interstitial hydrocarbons from the molecular sieve catalyst compositions. As shown, stripping medium is introduced into catalyst stripper 134 through line 135, and the resulting stripped stream 136 is released from catalyst stripper 134. Optionally, all or a portion of stripped stream 136 is directed back to fluidized reactor 102.

During contacting of the oxygenate feedstock with the molecular sieve catalyst composition in the fluidized reactor 102, the molecular sieve catalyst composition may become at least partially deactivated. That is, the molecular sieve catalyst composition becomes at least partially coked. In order to reactivate the molecular sieve catalyst composition, the catalyst composition preferably is directed to a catalyst regenerator 138. As shown, the stripped catalyst composition is transported, preferably in the fluidized manner, from catalyst stripper 134 to catalyst regenerator 138 in conduit 137. Preferably, the stripped catalyst composition is transported in a fluidized manner through conduit 137.

In catalyst regenerator 138, the stripped catalyst composition contacts a regeneration medium, preferably comprising oxygen, under conditions effective (preferably including heating the coked catalyst) to at least partially regenerate the catalyst composition contained therein. As shown, the regeneration medium is introduced into the catalyst regenerator 138 through line 139, and the resulting regenerated catalyst compositions are ultimately transported, preferably in a fluidized manner, from catalyst regenerator 138 back to the fluidized reactor 102 through conduit 141. The gaseous combustion products are released from the catalyst regenerator 138 through flue gas stream 140. In another embodiment, not shown, the regenerated catalyst composition additionally or alternatively is directed, optionally in a fluidized manner, from the catalyst regenerator 138 to one or more of the fluidized reactor 102 and/or the catalyst stripper 134. In one embodiment, not shown, a portion of the catalyst composition in the reaction system is transported directly, e.g., without first passing through the catalyst stripper 134, optionally in a fluidized manner, from the fluidized reactor 102 to the catalyst regenerator 138.

As the catalyst compositions contact the regeneration medium in catalyst regenerator 138, the temperature of the catalyst composition will increase due to the exothermic nature of the regeneration process. As a result, it is desirable to control the temperature of the catalyst composition by directing at least a portion of the catalyst composition from the catalyst regenerator 138 to a catalyst cooler 143, which is the subject of the present invention. As shown, the catalyst composition is transported in a fluidized manner from catalyst regenerator 138 to the catalyst cooler 143 through conduit 142. The resulting cooled catalyst composition is transported, preferably in a fluidized manner from catalyst cooler 143 back to the catalyst regenerator 138 through conduit 144. In another embodiment, not shown, the cooled catalyst composition additionally or alternatively is directed, optionally in a fluidized manner, from the catalyst cooler 143 to one or more of the fluidized reactor 102 and/or the catalyst stripper 134.

The processes and systems for cooling catalyst particles according to the present invention will now be described in greater detail.

C. Processes for Cooling Catalyst Particles

As indicated above, the present invention is directed to processes, systems and devices for cooling catalyst particles, preferably catalyst particles derived from an OTO reaction system. Preferably, the catalyst particles are derived from a catalyst regenerator in an OTO reaction system. A preferred embodiment of the present invention is a process for cooling catalyst, preferably catalyst in an oxygenate to olefins reaction system, wherein the process comprises the step of: (a) cooling a hot catalyst by superheating steam and boiling water to form a cold catalyst. As used herein, the terms "hot catalyst," "cool catalyst," and "cold catalyst" are relative to one another and are not limited to any particular temperature ranges. For example, hot catalyst has a temperature greater than cool catalyst, which has a temperature greater than cold catalyst.

It has now been discovered that certain catalyst compositions, particularly those implemented in OTO reaction processes, are particularly vulnerable to hydrothermal deactivation at temperatures below about 600° F. (316° C.). When such catalyst compositions come into contact with water at temperatures below about 600° F. (316° C.), many catalyst compositions become irreversibly deactivated. Certain silicoaluminophosphate molecular sieve catalyst compositions are particularly susceptible to hydrothermal deactivation. Catalyst compositions comprising SAPO-34 molecular sieves, which are commonly implemented in OTO reaction systems, are particularly susceptible to this hydrothermal deactivation.

One process for cooling catalyst particles comprises indirectly contacting the catalyst composition with water in a heat exchanger under conditions effective to cool the catalyst composition and boil the water to form steam. Unless otherwise indicated, "water" means liquid water. Boiling water to form steam is an efficient and practical means to cool molecular sieve catalyst compositions in OTO reaction system, particularly hot catalyst particles derived from OTO regenerators. As discussed above, it is desirable to maintain the cooling medium used to cool the catalyst composition at a temperature above 600° F. (316° C.) so that the catalyst particles cooled are not cooled below the threshold temperature for hydrothermal deactivation of 600° F. (316° C.). It is not practical, however, to maintain boiling water at such high temperatures because the boiler pressure required to maintain boiling water at or about this temperature would be in excess of 1500 psig (10,343 kPag). Manufacturing and maintaining heat exchangers capable of withstanding such high pressures would be prohibitively expensive. Thus, it has now been discovered that it is desirable to have a process for cooling catalyst particles, particularly catalyst particles derived from OTO regenerators, that would maintain the catalyst particles at a temperature above 600° F. (316° C.) at all points within the catalyst regeneration system without having to resort to ultra high pressure catalyst cooling systems.

In catalyst coolers in which water is the cooling medium, hot catalyst, preferably from a catalyst regenerator, is circulated through one side of the catalyst cooler and indirectly contacts water that is boiled on the other side of the catalyst cooler. Through this indirect contacting, heat is transferred from the hot catalyst particles contained in the catalyst cooler to the water thereby boiling the water and providing the necessary heat removal from the hot catalyst particles. Water boils at a constant temperature, and it can be expected that catalyst particles will be cooled to a temperature that approaches that of the boiling water under certain circumstances. The exchanger will, however, normally be designed to avoid cooling the catalyst to this low level at the design cooling rate.

There are circumstances where the required cooling rate is less than the design rate. These circumstances can include, but are not limited to, start-up situations, operation of an OTO reaction process with a lower than design coke yield (which reduces the cooling duty in the regenerator), operation with a low circulation rate of catalyst through the catalyst cooler, or a conservative design that provides extra heat transfer surface area. As indicated above, certain catalyst compositions are susceptible to hydrothermal deactivation when exposed to water vapor at temperatures below about 600° F. (316° C.). The pressure required to boil water at greater than 600° F. (316° C.) is in excess of 1500 psig (10,343 kPag). The construction of a catalyst cooler capable of withstanding such a high pressure would require very thick walls and would be very costly.

The present invention provides for the ability to cool hot catalyst particles to a temperature greater than 600° F. (316° C.). Specifically, the processes of the present invention and catalyst coolers for implementing same utilize boiling water and stream superheating to cool the hot catalyst particles and form cold catalyst particles.

The step of cooling the catalyst particles by superheating steam and boiling water may occur under a variety of conditions. In one embodiment, the cooling occurs at a pressure of from about 10 kpaa to about 10,000 kpaa, from about 50 kPaa to about 5,000 kPaa, or from about 100 kPaa to about 1,000 kPaa. Preferably, the pressure ranges from about 1,000 to about 5,000 kpaa. These pressures are on the cooling medium side (steam/water side) of the heat exchanger rather than the regenerator side. The hot catalyst preferably has a temperature of from about 400° C. to about 1000° C., more preferably from about 500° C. to about 900° C., and most preferably from about 600° C. to about 800° C. The cold catalyst has a temperature that is less than the temperature of the hot catalyst. The cold catalyst also preferably has a temperature of greater than about 316° C., more preferably greater than about 343° C., and most preferably greater than about 371° C. By maintaining the cold catalyst at a temperature greater than 316° C., hydrothermal deactivation can be minimized.

Figure 2:
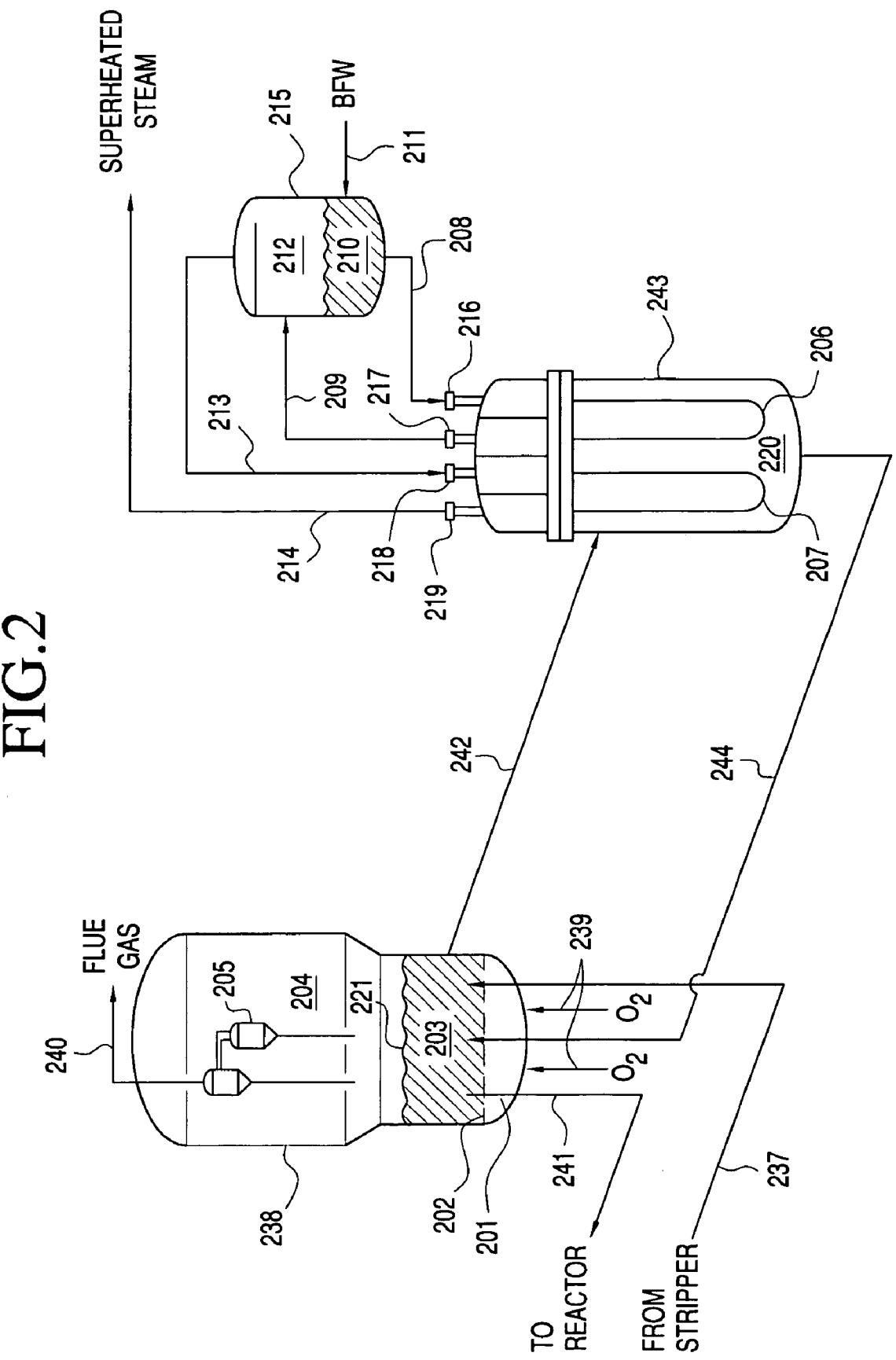
FIG. 2 illustrates a flow diagram of a catalyst regenerator in fluid communication with a catalyst cooler according to one embodiment of the present invention.

FIG. 2 presents a partial cross sectional view of a catalyst regenerator in fluid communication with a catalyst cooler according to one embodiment of the present invention. An at least partially coked catalyst composition is directed to catalyst regenerator 238 via stripped catalyst stream 237. Although it is preferred that the at least partially coked catalyst composition be directed from a catalyst stripper to catalyst regenerator 238, the at least partially coked catalyst composition received in catalyst regenerator 238 may be derived from virtually any device in the OTO reaction system. Preferably, stripped catalyst stream 237 is introduced directly into catalyst dense phase 203. In catalyst dense phase 203, the at least partially coked catalyst composition from stripped catalyst stream 237 contacts a regeneration medium, which is introduced into the catalyst regenerator 238 via one or more regeneration medium streams 239 (two are shown). As shown, regeneration medium streams 239 are introduced into a distribution zone 201, which is below catalyst dense phase 203. After being introduced into distribution zone 201, the regeneration medium is directed under pneumatic forces from the distribution zone 201 through distributor grid 202 and into catalyst dense phase 203. Distributor grid 202 preferably comprises a plate having a plurality of openings therethrough. The regeneration medium travels through these openings as it is directed from distribution zone 201 to catalyst dense phase 203.

In catalyst dense phase 203, the at least partially coked catalyst composition introduced via stripped catalyst stream 237 contacts the regeneration medium under conditions effective to at least partially regenerate the at least partially coked catalyst composition and form regenerated catalyst.

Thus, catalyst dense phase 203 comprises at least partially coked catalyst compositions and regenerated catalyst compositions. Preferably, an aliquot portion of the catalyst contained in catalyst dense phase 203 is withdrawn therefrom and directed back to the reactor through regenerated catalyst stream 241.

The regeneration process that occurs in catalyst dense phase 203 forms regenerated catalyst and regeneration byproducts, mostly gaseous byproducts such as carbon monoxide, water vapor and carbon dioxide. These gaseous byproducts of the regeneration process are transferred under pneumatic pressure from the catalyst dense phase 203 to dilute phase 204. A minor portion of the catalyst particles contained in catalyst dense phase 203 may become entrained with these gaseous byproducts of the regeneration process and also enter dilute phase 204. Most of the catalyst particles in dilute phase 204 will fall back into catalyst dense phase 203 due to gravitational effects. The gaseous byproducts in the dilute phase 204 and a minor portion of the catalyst particles in dilute phase 204 preferably enter one or more separation devices 205 in which the entrained catalyst compositions are separated from the gaseous byproducts of the regeneration process. Ultimately, the gaseous byproducts of the regeneration process are separated from the bulk of the entrained catalyst particles and yielded from the catalyst regenerator 238 as flue gas stream 240. The entrained catalyst particles in separation devices 205 preferably are separated from the gaseous byproducts and directed through one or more dip legs back to catalyst dense phase 203. Preferably, the separation devices 205 comprise cyclone separation vessels, although any of a number of other types of separation vessels may be used.

As indicated above, the process of regenerating an at least partially coked catalyst composition to form a regenerated catalyst composition is an exothermic process. As a result, after being introduced into the catalyst regenerator 238, the at least partially coked catalyst compositions contained in catalyst dense phase 203 will increase in temperature as the carbonaceous deposits on the at least partially coked catalyst compositions are combusted therefrom to form the regenerated catalyst composition.

In order to maintain the temperature of the catalyst particles contained in catalyst dense phase 203 at a desirable temperature, a portion of the catalyst particles contained in catalyst dense phase 203 preferably is removed for cooling and, after cooling, reintroduction back into catalyst regenerator 238. As shown, a portion of the catalyst particles contained in catalyst dense phase 203 is withdrawn therefrom and transferred via hot catalyst stream 242 to catalyst cooler 243. The outlet in catalyst regenerator 238 through which the hot catalyst exits the catalyst regenerator 238 and enters hot catalyst stream 242 preferably is situated below surface 221 of catalyst dense phase 203, as shown.

Catalyst cooler 243 is a heat exchanging device, preferably a shell and tube type heat exchanging device, but it may also be a jacketed pipe heat exchange device. Included in the category of shell and tube type heat exchange devices are bayonet tube (tube-inside-tube) exchangers and U-tube exchangers. As shown, catalyst cooler 243 includes a superheating steam cooling tube 207 and a boiling water cooling tube 206. Both the superheating steam cooling tube 207 and the boiling water cooling tube 206 are situated within a cooling zone 220. After being introduced into catalyst cooler 243, the hot catalyst from hot catalyst stream 242 contacts a first cooling surface on superheating steam cooling tube 207 and a second cooling surface on boiling water cooling tube 206 under conditions effective to cool the hot catalyst from hot catalyst stream 242 and form a cold catalyst. The cold catalyst, or a portion thereof, preferably is withdrawn from catalyst cooler 243 and directed back, preferably in a fluidized manner, to catalyst regenerator 238 as shown by cold catalyst stream 244. In other embodiments, not shown, the cold catalyst stream 244, or a portion thereof, is directed back to the reactor, not shown.

As indicated above, the cooling of the hot catalyst particles in catalyst cooler 243 preferably occurs by boiling water in boiling water cooling tube 206 and also by superheating steam in superheating steam cooling tube 207. As shown, water from separator drum 215 is directed from liquid phase 210 to water inlet 216 on catalyst cooler 243 via water stream 208. To make up for water removed from separator drum 215 via water stream 208, fresh water optionally is added to separator drum 215 via make up water stream 211, which preferably comprises boiler feed water. As the water travels through boiling water cooling tube 206 in the catalyst cooler 243, the water contained in boiling water cooling tube 206 preferably is boiled to form a water/steam stream 209, which is yielded from the catalyst cooler 243 via water/steam outlet 217. Water/steam stream 209 preferably comprises vaporized water. It is contemplated, however, that water/steam stream 209 may also comprise liquid water.

Water/stream 209 preferably is introduced into separator drum 215. As shown, the water/steam stream 209 is introduced into the gas phase 212 within separator drum 215, although water/steam stream 209 alternatively could be introduced into the liquid phase 210. Water vapor (steam) in gas phase 212 preferably is withdrawn from separator drum 215 via steam stream 213 and directed to steam inlet 218. Upon introduction into catalyst cooler 243, the steam from steam stream 213 preferably is directed through superheating steam cooling tube 207. As the steam from steam stream 213 travels through superheating steam cooling tube 207, the temperature of the steam contained in superheating steam cooling tube 207 preferably increases as the steam cools the hot catalyst in cooling zone 220.

The superheated steam formed in the cooling process is yielded from catalyst cooler 243 via superheated steam outlet 219. As shown, the superheated steam is yielded from the catalyst cooler 243 via superheated steam stream 214. The ultimate disposition of the superheated steam stream 214 may vary widely. Optionally, the superheated steam stream 214 is directed to a turbine, not shown, for the production of mechanical energy.

In one embodiment, the cooling occurs in one or more heat exchangers comprising a first cooling surface and a second cooling surface, wherein the first cooling surface has a first surface area dedicated to superheating steam and the second cooling surface has a second surface area dedicated to boiling water. In this embodiment, the ratio of the first surface area to the second surface area can be adjusted. For example, the ratio optionally is adjustable by moving a baffle located within a side of the one or more heat exchangers that divides steam superheating service from boiling water service. One non-limiting example of this embodiment is illustrated in FIG. 3A and FIG. 3B.

FIG. 3A and FIG. 3B illustrate this embodiment of the present invention. As shown, FIG. 3A illustrates catalyst cooler 343A in a first configuration in which two cooling tubes are dedicated to superheating steam and one cooling tube is dedicated to boiling water. One or more baffles located within catalyst cooler 343A are adjustable to adjust the ratio of the first surface area to the second surface area. FIG. 3B illustrates the catalyst cooler 343B in a second configuration in which two cooling tubes are dedicated to boiling water and one cooling tube is dedicated to superheating steam. Thus, in this embodiment, the number of cooling tubes dedicated to superheating steam and the number of cooling tubes dedicated to boiling water can be adjusted by moving one or more baffles from a first position to a second position.

As indicated above, FIG. 3A illustrates catalyst cooler 343A in a first configuration in which two cooling tubes are dedicated to superheating steam and one cooling tube is dedicated to boiling water. Specifically, the catalyst cooler 343A comprises a first cooling tube 366, which is dedicated to boiling water, and second and third cooling tubes 367 and 368, respectively, which are dedicated to superheating steam.

In operation, catalyst cooler 343A comprises a water inlet 316 through which water stream 308 is introduced into the catalyst cooler 343A. Specifically, in the configurations shown in FIG. 3, water stream 308 is introduced into water entrance zone 359A. After being introduced into water entrance zone 359A, the water is directed into inner tube 354A. Inner tube 354A preferably traverses separation plate 362 and separation plate 361 and extends into cooling zone 320, which is defined by outer shell 353 of catalyst cooler 343A/B. Thus, water from water entrance zone 359A is conveyed through inner tube 354A and is yielded therefrom through inner tube outlet 369.

After being yielded from inner tube 354A through inner tube outlet 369, the water is conveyed through outer tube 355A. Outer tube 355A preferably houses at least a portion of inner tube 354A in a manner such that the water can be conveyed through an annular space formed between the outer wall of inner tube 354A and the inner wall of outer tube 355A. As the water travels through the annular space between outer tube 355A and inner tube 354A, the water cools catalyst particles contained in cooling zone 320 through indirect contacting. Preferably, as the water in this annular space cools the catalyst particles in cooling zone 320, a portion of the water vaporizes. Thus, the catalyst particles contained in cooling zone 320 are cooled by boiling the water contained in the annular space. Ultimately, water and steam, preferably in equilibrium with one another, are yielded from the annular space formed between the outer tube 355A and inner tube 354A into water/steam exit zone 357A. After being yielded into water/steam exit zone 357A, the water and steam contained therein is directed through water/steam outlet 351 as shown by water/steam stream 309. Ultimately, the water/steam stream 309 preferably is directed to a separator drum, as shown in FIG. 2.

In the embodiment illustrated in FIG. 3A, second cooling tube 367 and third cooling tube 368 are dedicated to superheating steam. Steam in steam stream 313 is introduced into catalyst cooler 343A via steam inlet 318. Upon introduction into catalyst cooler 343A, steam from steam stream 313 enters steam entrance zone 360A. After being introduced into steam entrance zone 360A, the steam is directed into inner tubes 364A of second cooling tube 367 and third cooling tube 368. As shown, inner tubes 364A are in fluid communication with the steam entrance zone 360A and traverse separation plate 362 and separation plate 361. Thus, as discussed above with reference to inner tube 354A of first cooling tube 366, inner tubes 364A enter cooling zone 320.

In operation, the steam from steam entrance zone 360A enters inner tubes 364A and is conveyed therethrough, ultimately being released into the annular space formed between the outer surface of inner tubes 364A and the inner surface of outer tubes 365A. As the steam is directed through this annular space, preferably in an upward manner, the steam cools the catalyst particles contained in cooling zone 320 under conditions effective to superheat the steam contained in the annular space. Ultimately, superheated steam is yielded from the annular space into superheated steam exit zone 358A. One or more baffles 350A separate the water entrance zone 359A and the water/steam exit zone 357A from the steam entrance zone 360A and the superheated steam exit zone 358A, respectively. The superheated steam from superheated steam exit zone 358A then is yielded from the catalyst cooler 343A via superheated steam outlet 319 as shown by superheated steam stream 314. Superheated steam stream 314 optionally is directed to a turbine for the creation of mechanical energy.

Catalyst cooler 343A also comprises a hot catalyst inlet 363, which receives hot catalyst from a hot catalyst stream 342, preferably from a catalyst regenerator, not shown. Hot catalyst from hot catalyst stream 342 is introduced into cooling zone 320 in which the hot catalyst indirectly contacts the water in outer tube 355A and steam in outer tubes 365A under conditions effective to cool the hot catalyst and form cold catalyst. As the hot catalyst is cooled to form the cold catalyst in catalyst cooler 343A, the catalyst particles are directed to conical section 356 which acts to direct the cold catalyst particles to cold catalyst outlet 352. Ultimately, cold catalyst particles are yielded from cold catalyst outlet 352 in catalyst cooler 343A as shown by cold catalyst stream 344.

It may be desirable under certain circumstances to change the cooling characteristics of the catalyst cooler 343A. For example, an increase in the rate of carbonaceous compounds formed in the OTO reactor would require additional cooling duty in the regenerator. On the other hand, a decrease in the rate of formation of carbonaceous compounds in the OTO reactor would result in a reduction in the cooling duty required in the regenerator. In the first case, the regeneration temperature may be higher than desired, and in the second case, the catalyst temperature in the catalyst cooler may be lower than desired. When it is desired to change the cooling characteristics of catalyst cooler 343A, then the ratio of the first surface area to the second surface area can be adjusted. As shown, the ratio is adjustable by moving baffle 350A from the configuration shown in FIG. 3A to, for example, the configuration of baffle 350B, shown in FIG. 3B. The moving of the baffle 350A optionally occurs during operation or alternatively prior to operation of the heat exchanger. As the baffle is transitioned from the configuration illustrated in FIG. 3A to the configuration illustrated in FIG. 3B, the number of cooling tubes that are dedicated to boiling water and the number of cooling tubes that are dedicated to superheating steam is altered. As shown, FIG. 3A illustrates that the water from water stream 308 is introduced into first cooling tube 366 while steam from steam stream 313 is introduced into the second cooling tube 367 and the third cooling tube 368. As baffle 350A is moved to the configuration illustrated in FIG. 3B, however, the water from water stream 308 is directed to the second cooling tube 367 in addition to the first cooling tube 366, while the steam from steam stream 313 is introduced solely into third cooling tube 368. Since boiling water heat transfer surface provides more effective cooling than steam superheat surface, the configuration of FIG. 3B will provide more cooling than the configuration of FIG. 3A.

In terms of surface area, the first cooling surface area, which is dedicated to superheating steam, is illustrated in FIG. 3A as the outer surface of outer tubes 365A of the second cooling tube 367 and third cooling tube 368. The second cooling surface area, which is dedicated to boiling water, is illustrated in FIG. 3A as the outer surface of outer tube 355A of first cooling tube 366. Since the first cooling surface area illustrated in FIG. 3A is roughly twice the second cooling surface area, the ratio of the first cooling surface area to the second cooling surface area is about 2.0.

As the baffle 350A/B is moved from the configuration of baffle 350A to the configuration of baffle 350B, however, the surface areas dedicated to boiling water and superheating steam are altered. Specifically, as shown in FIG. 3B, the first cooling surface area comprises the outer surface of outer tube 365B of the third cooling tube 368. The second cooling surface area comprises the outer surface of outer tubes 355B of first cooling tube 366 and second cooling tube 367. Since the first cooling surface area illustrated in FIG. 3B is roughly half of the second cooling surface area, the ratio of the first cooling surface area to the second cooling surface area is about 0.5.

The embodiment illustrated in FIG. 3A and FIG. 3B is exemplary and the present invention is not limited to catalyst coolers comprising three cooling tubes or to processes for using same. It is contemplated, for example, that the catalyst cooler may comprise two cooling tubes. In this embodiment, one cooling tube may be dedicated to boiling water and the other dedicated to superheating steam. Alternatively, both of the tubes may be dedicated to boiling water or both may be dedicated to superheating steam. Preferably, however, the catalyst cooler that implements this embodiment of the present invention comprises many cooling tubes, e.g., four, five, six, or many more cooling tubes.

Additionally, it is contemplated that a catalyst cooler may have a plurality of different configurations. In one embodiment, not shown, the baffle may be moved so as to dedicate all of the cooling tubes to either steam superheating service or boiling water service. For example, if the catalyst cooler comprises four cooling tubes, it is contemplated that the catalyst cooler may operate with all four of the cooling tubes being dedicated to boiling water or, in the alternative, to superheating steam. It is further contemplated that such a catalyst cooler may be configured to boil water in a single cooling tube and superheat steam in the remaining three cooling tubes. Similarly, it is contemplated that one of the cooling tubes may be dedicated to superheating steam, and the remaining three cooling tubes may be dedicated to boiling water. Further, it is contemplated that two of the cooling tubes in such a catalyst cooler may be dedicated to superheating steam and the remaining two cooling tubes may be dedicated to boiling water. Similar cooling configurations can be achieved with catalyst coolers having many more cooling tubes.

Additionally or alternatively, the ratio of the first surface area to the second surface area is adjustable by dividing the one or more heat exchangers into a plurality of zones, wherein one or more of the zones can be piped into either steam superheating service or boiling water service. One non-limiting example of this embodiment is illustrated in FIG. 4A and FIG. 4B.

FIG. 4A and FIG. 4B illustrate two different configurations of a catalyst cooling system according to this embodiment of the present invention. In this embodiment, the catalyst cooler 443A/B comprises a plurality of cooling tubes, which define a plurality of cooling zones that can be piped into either steam superheating service or boiling water service. As shown, catalyst cooler 443A/B comprises a first cooling tube 466, a second cooling tube 467 and a third cooling tube 468, all of which are housed within shell 453 defining cooling zone 420. Each cooling tube has a respective surface area associated therewith. According to the embodiment illustrated in FIG. 4A and FIG. 4B, the surface area in the catalyst cooler 443A/B that is dedicated to superheating steam can be adjusted. Accordingly, the surface area within catalyst cooler 443A/B that is dedicated to boiling water can also be adjusted.

In this embodiment, the ratio of the surface area dedicated to superheating steam to the surface area dedicated to boiling water is adjusted by opening and/or closing one or more valves in the catalyst cooling system and thereby adjusting the flow of the steam and water (cooling mediums) that is directed to the several zones within catalyst cooler 443A/B. Specifically, the ratio is adjustable by providing a catalyst cooler 443A/B having a plurality of cooling zones, wherein one or more of the cooling zones can be piped into either steam superheating service or boiling water service.

FIG. 4A illustrates a first configuration of this embodiment of the present invention. In the configuration illustrated in FIG. 4A, water is piped into first cooling tube 466 and second cooling tube 467, and steam is piped into third cooling tube 468. In the configuration illustrated in FIG. 4B, however, water is piped into first cooling tube 466, and steam is piped into second cooling tube 467 and third cooling tube 468.

Although many various configurations are possible for adjusting which zones in a catalyst cooler are dedicated to steam superheating and boiling water, one possible configuration is illustrated in FIG. 4A and FIG. 4B. As shown, water in water stream 471 is separated into a plurality of derivative streams 473 and 478, both of which are directed to catalyst cooler 443A. Specifically, derivative stream 473 is directed to first entrance zone 494, and derivative stream 478 is directed to second entrance zone 495. The flow of water from water stream 471 is controlled by a series of valves 472 and 474A, as shown. In the configuration illustrated in FIG. 4A, valves 472 and 474A are in an open positions. In this configuration, water in water stream 471 is in a closed communication with steam from steam stream 477. Steam from steam stream 477 is ultimately directed to third entrance zone 496 via derivative stream 479, as shown. As with water stream 471, the flow rate of the steam in steam stream 477 is controlled by a series of valves. As shown, valve 476, which is in an open configuration, allows the steam from steam stream 477 to flow to derivative stream 479. As shown, water stream 471 is in closed communication with steam stream 477, which means that a single closed valve operates to separate the flow of the water in water stream 471 from steam in steam stream 477. In the embodiment illustrated in FIG. 4A, valve 475A is in a closed position thereby preventing steam in steam stream 477 from commingling with water in water stream 471.

As indicated above, catalyst cooler 443A/B comprises a plurality of cooling zones. Each of these cooling zones may be piped into steam superheating duty or boiling water duty. Each zone preferably is separated by one or more baffles from the other cooling zones in catalyst cooler 443A/B. As shown, first entrance zone 494 is separated from second entrance zone 495 by baffle 492, and second entrance zone 495 is separated from third entrance zone 496 via baffle 493. Similarly, first exit zone 497 is separated from second exit zone 498 by first baffle 492, and second exit zone 498 is separated from third exit zone 499 by baffle 493. Interior cooling zones, for example second entrance zone 495 and second exit zone 498 preferably include one or more exit conduits for conveying water/steam or superheated steam, depending on whether water or steam is piped into the interior zone, away from the catalyst cooler 443A/B, e.g., to a separator drum, as illustrated in FIG. 2.

As with the embodiment illustrated in FIG. 3A/B, water and/or steam is conveyed through the cooling tubes in catalyst cooler 443A/B to provide indirect contacting with hot catalyst in catalyst cooler 443A/B received from hot catalyst stream 442 via hot catalyst inlet 463. Once inside catalyst cooler 443A/B, the indirect contacting with the water and/or steam in the cooling tubes causes the hot catalyst to be cooled and form cold catalyst which is directed by conical section 456 to cold catalyst outlet 452. The cold catalyst is ultimately yielded from the catalyst cooler 443A/B as shown by cold catalyst stream 444.

After flowing through first cooling tube 466, water and steam is directed to first exit zone 497 and released from the catalyst cooler 443A via water/steam outlet 451. Similarly, water and steam from second cooling tube 467 is directed to second exit zone 498. The water and steam in second exit zone 498 enters inlet 491 of conduit 483. Ultimately, the water and steam from second exit zone 498 is yielded from the catalyst cooler 443A via water/steam stream 484. Water/steam stream 484 is then directed as derivative stream 485 through open valve 487A and combined with water/steam stream 409 from water/steam outlet 451 to form a combined water/steam stream 489. Combined water/steam stream 489 preferably is directed to a separator drum, not shown, but illustrated in FIG. 2.

In the configuration shown at FIG. 4A, the superheated steam from third cooling tube 468 is directed to third exit zone 499. The superheated steam in third exit zone 499 is released from the catalyst cooler 443A via superheated steam outlet 419. Specifically, superheated steam is yielded from the catalyst cooler 443A as superheated steam stream 414. As shown, valve 488A is in a closed position in the configuration shown in FIG. 4A so as to prevent commingling of the water and steam from water/steam stream 484 with the superheated steam that is released from the catalyst cooler 443A in superheated steam stream 414.

FIG. 4B illustrates a second configuration in which two cooling tubes are dedicated to superheating steam and one cooling tube is dedicated to boiling water. Specifically, as shown, water is directed through open valve 472 and derivative stream 473 into first entrance zone 494. As with the configuration in FIG. 4A, the water in first entrance zone 494 is directed to first cooling tube 466 and ultimately yielded from the catalyst cooler 443B via water/steam outlet 451 as water/steam stream 409. In this configuration, the water/steam stream 409 is not combined with any other stream since only one of the cooling tubes is dedicated to boiling water.

Further, in the configuration illustrated in FIG. 4B, steam in steam stream 477 passes through open valve 476 and open valve 475B to form derivative streams 478 and 479. Derivative streams 478 and 479 are direct to second entrance zone 495 and third entrance zone 496, respectively. Thus, steam from steam stream 477 ultimately enters second cooling tube 467 and third cooling tube 468. After passing through second cooling tube 467, superheated steam enters second exit zone 498, which is interiorly situated with respect to first exit zone 497 and third exit zone 499. The superheated steam in second exit zone 498 is directed into inlet 491 and through conduit 483 to form superheated steam stream 484. Superheated steam stream 484 then passes through open valve 488B as stream 486 which is combined with superheated steam stream 414 to form combined superheated steam stream 490. In the configuration shown in FIG. 4B, valve 487B is in a closed configuration so as to prevent commingling of superheated steam from superheated steam stream 484 with water/steam stream 409. Additionally, valve 474B is in a closed position so as to prevent commingling of water from water stream 471 with steam from steam stream 477.

In other embodiments, not shown, all of the cooling zones in the catalyst cooler may be dedicated to boiling water or superheating steam. In other embodiments, not shown, the catalyst cooler comprises several different cooling zones, e.g. 5, 6, 7 or more cooling zones so as, to allow many different possible cooling configurations.

In the embodiment shown in FIG. 4A and FIG. 4B, baffles 492 and baffles 493 preferably are stationary, e.g., not adjustable. That is, the baffles preferably do not move within the catalyst cooler 443A/B so as to vary the flow of the cooling medium therein (for example as shown in FIG. 3A and FIG. 3B). It is contemplated, however, that the adjustable baffle embodiment disclosed in FIG. 3A and FIG. 3B may be combined with the adjustable piping embodiment disclosed in FIG. 4A and FIG. 4B.

In another embodiment of the present invention, the ratio of surface area that is dedicated to superheating steam to the surface area that is dedicated to boiling water is adjustable by providing a plurality of heat exchangers, wherein one or more of the plurality of heat exchangers can be piped into either steam superheating service or boiling water service. One nonlimiting example of this embodiment of the present invention is illustrated in FIG. 5.

Figure 5:
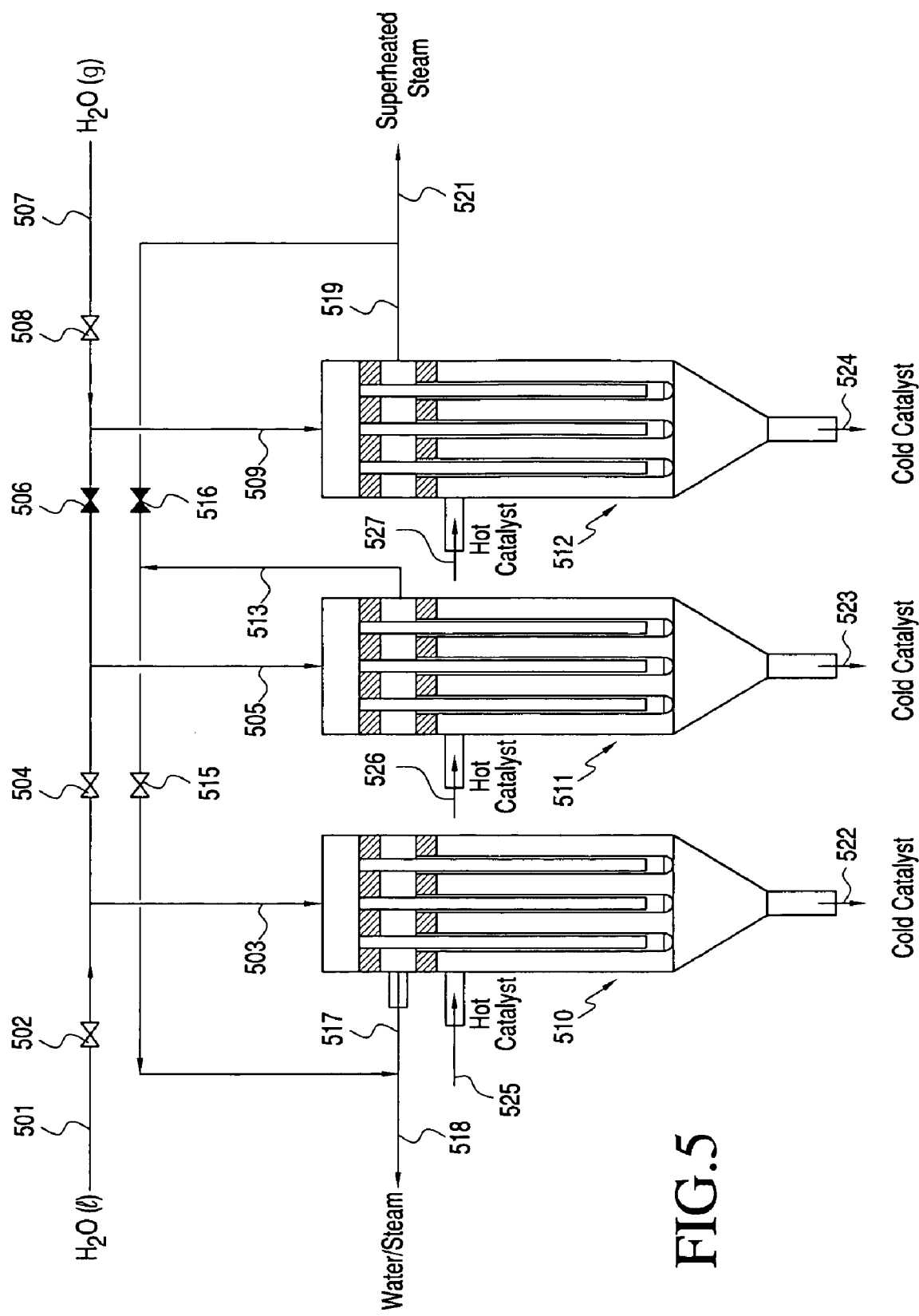
FIG. 5 illustrates a catalyst cooling system, which comprises a plurality of catalyst coolers in a first configuration according to another embodiment of the present invention.

FIG. 5 illustrates a catalyst cooling system comprising three catalyst coolers 510, 511 and 512, each of which can be dedicated to either boiling water service or superheating steam service. As shown, catalyst cooler 510 and catalyst cooler 511 are dedicated to boiling water service and catalyst cooler 512 is dedicated to superheating steam service.

Specifically, water in water stream 501 is directed through open valve 502 and separated into derivative stream 503 and derivative stream 505. Valve 504, which is in an open configuration in FIG. 5, controls the flow of water from water stream 501 to derivative stream 505. Derivative stream 503 is in fluid communication with catalyst cooler 510, and derivative stream 505 is in fluid communication with catalyst cooler 511.

Water from derivative stream 503 enters catalyst cooler 510 and cools hot catalyst from hot catalyst stream 525 in an indirect contacting manner to form cold catalyst which is yielded from catalyst cooler 510 via cold catalyst stream 522. As the hot catalyst is cooled in catalyst cooler 510, water in the cooling tubes within catalyst cooler 510 is boiled to form water/steam stream 517, which is yielded from catalyst cooler 510. In the configuration illustrated in FIG. 5, catalyst cooler 511 operates in a manner substantially similar to catalyst cooler 510 to cool hot catalyst from hot catalyst stream 526 and form cold catalyst in cold catalyst stream 523. The water and steam formed in the cooling process within catalyst cooler 511 is yielded therefrom in water/steam stream 513. Water/steam stream 513 is then directed to open valve 515 and combined with water/steam stream 517 to form combined water/steam stream 518.

Simultaneously, steam from steam stream 507 passes through open valve 508 to form derivative stream 509, which is directed to catalyst cooler 512. Thus, catalyst cooler 512 is dedicated to superheating steam as hot catalyst from hot catalyst stream 527 is cooled to form cold catalyst stream 524. The superheated steam formed in the cooling process within catalyst cooler 512 preferably is yielded therefrom as superheated steam stream 519.

In the configuration illustrated in FIG. 5, valve 506 is in a closed position so as to prevent commingling of steam from steam stream 507 with water from water stream 501. Similarly, valve 516 is in a closed configuration so as to prevent commingling of water/steam from water/steam stream 513 with superheated stream yielded from catalyst cooler 512 in superheated steam stream 519.

As indicated above, in the embodiment shown in FIG. 5, the ratio of surface area dedicated to steam superheating to the surface area dedicated to boiling water can be adjusted by opening and closing one or more valves so as to change one or more of the catalyst coolers contained in the catalyst cooling system from steam superheating service to boiling water service, or vice-a-versa. For example, valve 504 may be closed and valve 506 may be opened so as to deliver steam from steam stream 507 to catalyst coolers 511 and 512 via derivative stream 505 and derivative stream 509. In this manner, catalyst cooler 511 and catalyst cooler 512 can be dedicated to superheating steam service, and catalyst cooler 510 can be dedicated to boiling water service. In this embodiment, valve 515 should be closed and valve 516 should be opened so as to prevent commingling of superheated steam from superheated steam stream 513 with water/steam from water/steam stream 517. Thus, superheated steam from superheated steam stream 513 is directed through open valve 516 and combined with superheated steam from superheated steam stream 519 to form combined superheated steam stream 521.

In another embodiment, not shown, valve 502 may be closed and valves 504, 506 and 508 may be opened so as to allow steam from steam stream 507 to enter each of catalyst coolers 510, 511 and 512. In this manner, each of the catalyst coolers can be dedicated to superheating steam service rather than boiling water service. It is preferred in this embodiment that each of valves 515 and 516 are open so as to allow superheated steam formed in catalyst cooler 511 to commingle with superheated steam from both catalyst cooler 510 and catalyst cooler 512.

In another embodiment, not shown, each of the three catalyst coolers 510, 511 and 512 are dedicated to boiling water service. In this embodiment, valves 502, 504 and 506 are in an open position, and valve 508 is in a closed position. This configuration allows water from water stream 501 to flow through derivative streams 503, 505, and 509 and into each of catalyst coolers 510, 511 and 512. It is preferred in this embodiment that valves 515 and 516 be in an open position so as to allow the water/steam in water/steam stream 513 to commingle with the water/steam that is yielded from catalyst cooler 510 and catalyst cooler 512.

The present invention will be better understood in view of the following non-limiting examples.

D. EXAMPLE I (COMPARATIVE)

In Example I, temperature profiles were determined for four hot catalyst particle samples (A-D) that were cooled in a catalyst cooler by indirectly contacting water under conditions effective to boil the water. In this prophetic example, the water was allowed to boil at a constant temperature of 490° F. (254° C.) and at a pressure of 600 psig (4,137 kPag). The catalyst inlet temperature was 1200° F. (649° C.) for each case as this temperature approximated the temperature of hot catalyst particles that are yielded from OTO catalyst regenerators. The total surface area in the catalyst cooler of this example was 100 ft$^2$ (9.290 m$^2$), all of which was dedicated to boiling water service. The heat transfer coefficient for this example is 100 Btu/hr-ft$^2$-° F. (567 J/ s-m$^2$-°K). In this example, the cooling duty of the catalyst cooler was controlled by varying the flow of the hot catalyst particles through the catalyst cooler. If less cooling was desired, the flow of the hot catalyst particles through the catalyst cooler was reduced. This reduction in catalyst flow results in a reduction in the temperature of the cold catalyst particles exiting the catalyst cooler. The cooling provided by the returning catalyst is a function of both the temperature and the flow rate. As a result, a greater than proportional reduction in the flow rate is required to achieve a given reduction in cooling duty.

In this example, the temperatures of the cold catalyst particles exiting the catalyst cooler were calculated as a function of catalyst cooler surface area dedicated to boiling water at 490° F. (254° C.). These cold catalyst temperatures were determined at catalyst cooler cooling duties ranging from 48% to 100% according to the following equation:

$$\frac{dT_{hot}}{dA} = \frac{U_o}{M C_p}(T_{hot} - T_{cold}) \quad (1)$$

wherein $T_{hot}$=hot side temperature (° C.),
$T_{cold}$=cold side temperature (° C.),
A=surface area in catalyst cooler dedicated to boiling water (m$^2$), $U_o$=heat transfer coefficient=100 Btu/hr-ft$^2$-° F. (567 J/s-m$^2$-° K.), M=mass flow rate of catalyst (kg/hr), and $C_p$=heat capacity of catalyst=0.22 Btu/lb-° F. (920 J/kg-° K.).

Table I, below, shows the catalyst flow rate, exchanger duty, hot stream inlet temperature, cold catalyst temperature and cold stream temperature for each of cases A through D. As shown, the cold catalyst particles' temperature fell below the 600° F. (316° C.) minimum temperature in case C, which operates at 60% of design duty, as well as for case D, which operates at 48% of design duty.

Figure 6:
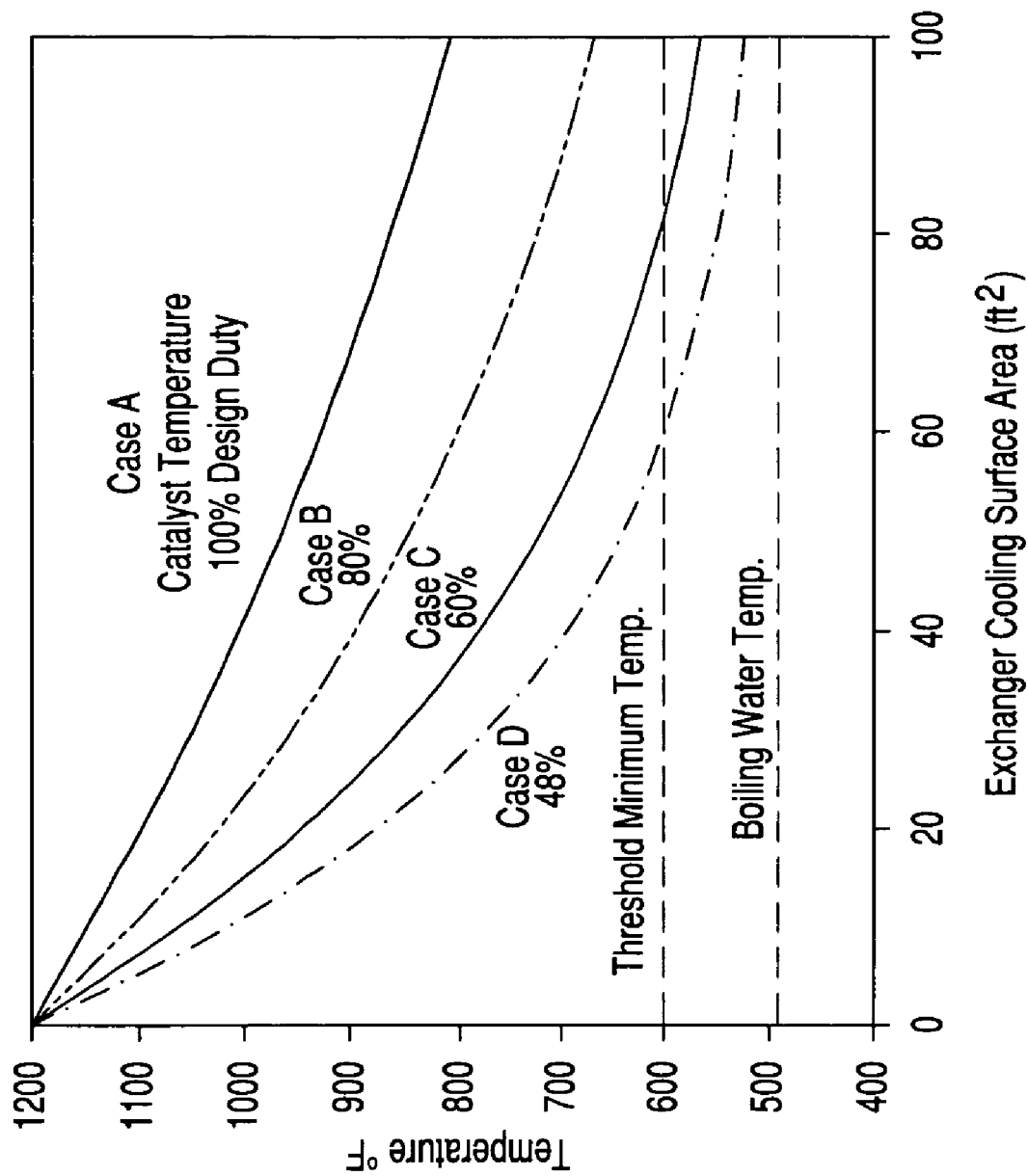
FIG. 6 presents a graph plotting heat exchanger surface area against cooled catalyst temperature for cases A-D of Example I.

These cases are undesirable because the catalyst particles fell below the minimum acceptable threshold temperature for many OTO molecular sieves and may undesirably facilitate hydrothermal deactivation of the cold catalyst particles. The graph in FIG. 6 illustrates how the cold catalyst temperature changes with surface area dedicated to boiling water for each of cases A through D. As shown in FIG. 6 and Table I, it would be highly desirable to provide a catalyst cooling system that would allow a greater turn-down in catalyst cooler duty without cooling hot catalyst particles to temperatures below the minimum threshold temperature of 600° F. (316° C.).

TABLE I

Boiling Water Catalyst Cooler Calculations

| Case | Catalyst Flow Rate lb/hr (kg/hr) | Exchanger Duty, MBtu/hr (MJ/hr) (% of design) | Hot Catalyst Temperature ° F. (° C.) | Cold Catalyst Temperature ° F. (° C.) | Cooling Medium Temperature ° F. (° C.) |
|---|---|---|---|---|---|
| A | 58,467 (26,520) | 5.0 (5270) (100%) | 1200 (649) | 811 (433) | 490 (254) |
| B | 34,336 (15,575) | 4.0 (4216) (80%) | 1200 (649) | 670 (354) | 490 (254) |
| C | 25,512 (11,572) | 3.0 (3162) (60%) | 1200 (649) | 566 (297) | 490 (254) |
| D | 16,140 (7,321) | 2.4 (2530) (48%) | 1200 (649) | 524 (273) | 490 (254) |

E. EXAMPLE II

Example II provides four cases (E-H) in which hot catalyst particles at a temperature of 1200° F. (649° C.) were cooled in a catalyst cooler system shown in FIG. 2 (note, however, that case E was not achievable). In this embodiment, 50% of the cooling surface area in the catalyst cooler was dedicated to boiling water and the other 50% of the cooling surface area in the catalyst cooler was dedicated to superheating steam. The calculations for cooling hot catalyst particles by boiling water are described above with reference to equation (1). The cooling duty provided by steam superheating is dictated by the following equation, which describes the energy change across the cooling surface dedicated to steam superheating:

$$\frac{dQ}{dA} = U_o(T_{hot} - T_{cold}) \quad (2)$$

The temperature profile for the superheating steam can then be described with equation (3).

$$\frac{dT_{cold}}{dA} = \left(\frac{1}{M_{steam}C_{pstm}}\right)\left(\frac{dQ}{dA}\right) \qquad (3)$$

wherein Q=Energy rate, Btu/hr (J/hr)

$M_{steam}$=mass flow rate of steam, lb/hr (kg/hr), and $C_{Pstm}$=Heat capacity of steam=0.79 Btu/lb-° F. (3302 J/kg-° K.)

Figure 7:
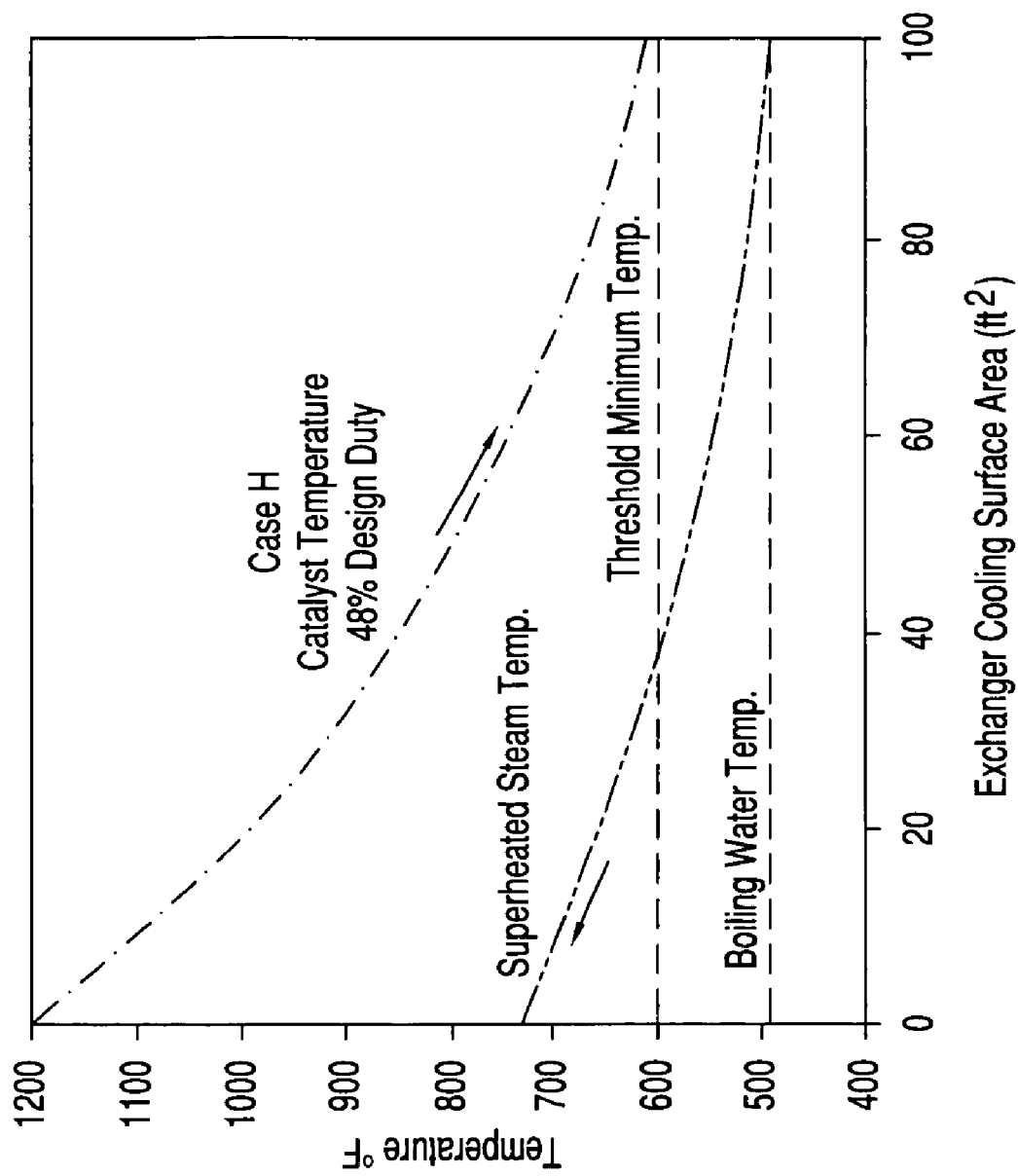
FIG. 7 presents a graph plotting heat exchanger surface area against cooled catalyst temperature for case H of Example II.

Table II, below, provides cold catalyst temperatures for three cases ranging in exchanger duty from 48% to 80%. Note that an exchanger duty of 100% is not achievable in this configuration as shown by case E. FIG. 7 provides a graph showing how cold catalyst temperature changes as a function of percent surface area dedicated to boiling water and superheating steam for case H (48% design duty). The temperature profiles for both boiling water and superheating steam in the catalyst cooler are shown. The heat transfer coefficient for the steam superheating surface area is 75 Btu/hr-ft²-° F. (425 J/s-m²-°K). This coefficient is lower than the coefficient in the boiling regime, 100 Btu/hr-ft²-° F. (567 J/s-m²-°K), because heat is transferred more easily to boiling water than it is to superheated gas.

As shown in FIG. 7, the cool catalyst that is yielded from the catalyst cooler at 48% design duty does not drop below the 600° F. (316° C.) threshold minimum temperature. By comparison, when all cooling duty was conducted with boiling water, as shown in Example I, the cold catalyst yielded from the catalyst cooler was 524° F. (273° C.), well below the 600° F. (316° C.) threshold minimum temperature. Specifically, the cold catalyst yielded from the catalyst cooler in case H of Example II was 612° F. (322° C.) using boiling water and steam superheating to cool the hot catalyst particles. Thus, catalyst particles cooled according to the present invention provide ideal cooling characteristics superior to those of boiling water alone—particularly when the catalyst cooler operated at reduced duties.

The temperature profiles provided in FIG. 7 are for a theoretical catalyst cooler having 50% surface area dedicated to boiling water and 50% surface area dedicated to superheating steam at a 48% of design duty (case H). The total cooling surface area is the same as in cases A-D of Example I.

Case E in Example II, which operates at 100% design efficiency, is not achievable without using boiling water over the entire cooling surface area. Cases F through H, however, are all feasible and result in catalyst outlet temperatures that are above the 600° F. (316° C.) minimum threshold temperature.

TABLE II

Boiling Water & Steam Superheating Catalyst Cooler Calculations

| Case | Catalyst Flow Rate lb/hr (kg/hr) | Exchanger Duty, MBtu/hr (MJ/hr) (% of design) | Hot Catalyst Temperature ° F. (° C.) | Cold Catalyst Temperature ° F. (° C.) | Cooling Medium Temperature ° F. (° C.) |
|---|---|---|---|---|---|
| E | Not Achievable | 5.0 (5270) (100%) | 1200 (649) | N/A | N/A |
| F | 69,296 (31,432) | 4.0 (4216) (80%) | 1200 (649) | 938 (503) | 490 (254) |
| G | 28,087 (12,740) | 3.0 (3162) (60%) | 1200 (649) | 714 (379) | 490 (254) |
| H | 18,549 (8,414) | 2.4 (2530) (48%) | 1200 (649) | 612 (322) | 490 (254) |

While various embodiments of the present invention have been described in detail, it is apparent that modifications and adaptations of those embodiments will occur to those skilled in the art. It is to be expressly understood, however, that such modifications and adaptations are within the spirit and scope of the present invention.

We claim:

1. A process for regenerating catalyst, wherein the process comprises the steps of:
    (a) regenerating an at least partially coked catalyst particle to form a regenerated catalyst particle having a temperature greater than about 593° C.; and
    (b) cooling the regenerated catalyst particle by at least about 38° C. through superheating steam and boiling water, but to a temperature of no less than 316° C., at a regeneration pressure of less than about 10,343 kPag, to form a cold catalyst;
    wherein the cooling occurs in one or more heat exchangers comprising a first cooling surface and a second cooling surface, the first cooling surface having a first surface area dedicated to superheating steam and the second cooling surface having a second surface area dedicated to boiling water, and wherein the ratio of the first surface area to the second surface area can be adjusted.

2. The process of claim 1, wherein the ratio is adjustable by moving a baffle located within a side of the one or more heat exchangers that divides steam superheating service from boiling water service.

3. The process of claim 1, wherein the ratio is adjustable by dividing the one or more heat exchangers into a plurality of zones, wherein one or more of the zones can be piped into either steam superheating service or boiling water service.

4. The process of claim 1, wherein the ratio is adjustable by providing a plurality of heat exchangers, wherein one or more of the plurality of heat exchangers can be piped into either steam superheating service or boiling water service.

5. The process of claim 1, wherein the regenerated catalyst and the cold catalyst comprise a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, AEI/CHA intergrowths, mixtures thereof, and metal containing forms thereof.

6. The process of claim 1, wherein step (b) comprises the sub-steps of:
    (i) cooling the regenerated catalyst by superheating steam to form a cool catalyst; and
    (ii) cooling the cool catalyst by boiling water to form the cold catalyst.

7. The process of claim 6, wherein sub-step (i) occurs before sub-step (ii).

8. The process of claim 6, wherein sub-steps (i) and (ii) occur simultaneously.

9. The process of claim 6, wherein sub-steps (i) and (ii) occur in separate heat exchangers.

10. The process of claim 6, wherein sub-steps (i) and (ii) occur in a single heat exchanger.

11. The process of claim 6, wherein sub-steps (i) and (ii) occur at a pressure of from about 10 kPaa to about 10,000 kPaa.

12. The process of claim 11, wherein sub-steps (i) and (ii) occur at a pressure of from about 50 kPaa to about 5,000 kPaa.

13. The process of claim 12, wherein sub-steps (i) and (ii) occur at a pressure of from about 100 kPaa to about 1,000 kPaa.

14. The process of claim 6, wherein the regenerated catalyst has a temperature of from about 400° C. to about 1000° C.

15. The process of claim 14, wherein the regenerated catalyst has a temperature of from about 500° C. to about 900° C.

16. The process of claim 15, wherein the regenerated catalyst has a temperature of from about 600° C. to about 800° C.

17. The process of claim 6, wherein the cold catalyst has a temperature of greater than about 316° C.

18. The process of claim 17, wherein the cold catalyst has a temperature of greater than about 343° C.

19. The process of claim 18, wherein the cold catalyst has a temperature of greater than about 371° C.

20. The process of claim 6, wherein the process further comprises the step of:
  (c) directing the cold catalyst back to the catalyst regenerator.

* * * * *